United States Patent
Foster

(10) Patent No.: US 12,004,671 B2
(45) Date of Patent: Jun. 11, 2024

(54) TEMPERATURE-CONTROLLED DELIVERY BOX WITH SANITIZATION ASSEMBLY AND SECURITY FEATURES

(71) Applicant: Haier US Appliance Solutions, Inc., Wilmington, DE (US)

(72) Inventor: Ronald Gary Foster, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 831 days.

(21) Appl. No.: 17/094,168

(22) Filed: Nov. 10, 2020

(65) Prior Publication Data

US 2022/0142388 A1     May 12, 2022

(51) Int. Cl.
| | |
|---|---|
| *A61L 2/20* | (2006.01) |
| *A47G 29/14* | (2006.01) |
| *A61L 2/10* | (2006.01) |
| *A61L 2/24* | (2006.01) |
| *A61L 101/02* | (2006.01) |

(52) U.S. Cl.
CPC .............. *A47G 29/141* (2013.01); *A61L 2/10* (2013.01); *A61L 2/202* (2013.01); *A61L 2/24* (2013.01); *A47G 2029/142* (2013.01); *A47G 2029/145* (2013.01); *A47G 2029/147* (2013.01); *A61L 2101/02* (2020.08); *A61L 2202/11* (2013.01); *A61L 2202/121* (2013.01); *A61L 2202/122* (2013.01); *A61L 2202/14* (2013.01)

(58) Field of Classification Search
CPC ............ A47G 29/141; A47G 2029/142; A47G 2029/145; A47G 2029/147; A47G 2029/144; A47G 2029/149; A61L 2/10; A61L 2/202; A61L 2/24; A61L 2101/02; A61L 2202/11; A61L 2202/121; A61L 2202/122; A61L 2202/14; A61L 2202/16; A61L 2202/182
USPC ........................................................ 422/105
See application file for complete search history.

(56) References Cited

U.S. PATENT DOCUMENTS

| | | | |
|---|---|---|---|
| 2015/0371513 A1* | 12/2015 | Stokes | G08B 17/06 340/589 |
| 2019/0387910 A1 | 12/2019 | Stoich | |
| 2020/0121088 A1 | 4/2020 | Chasnis, II | |

FOREIGN PATENT DOCUMENTS

| | | | |
|---|---|---|---|
| CN | 104670163 A | * | 6/2015 |
| KR | 200406801 Y1 | * | 1/2006 |
| KR | 101489296 B1 | * | 2/2015 |

(Continued)

OTHER PUBLICATIONS

Machine translations of KR-101700194 B1, KR-101489296 B1, KR-200406801 Y1, CN-104670163 A (Year: 2023).*

*Primary Examiner* — Huy Tram Nguyen
(74) *Attorney, Agent, or Firm* — Dority & Manning, P.A.

(57) ABSTRACT

A temperature controlled delivery appliance and a method of operating the same are provided. The temperature-controlled delivery appliance includes a storage container, a climate control system, a sanitization assembly, and a locking mechanism. The sanitization assembly may include an ultraviolet light assembly or an ozone generator that may be selectively activated after a delivery to sanitize the delivered items. The locking mechanism locks the door of the temperature-controlled delivery appliance to prevent user access during a sanitization cycle, as well as to prevent other unauthorized access.

19 Claims, 9 Drawing Sheets

(56) References Cited

FOREIGN PATENT DOCUMENTS

| KR | 101489296 | B1 | | 2/2015 |
| KR | 101700194 | B1 | * | 1/2017 |

* cited by examiner

US 12,004,671 B2

TEMPERATURE-CONTROLLED DELIVERY BOX WITH SANITIZATION ASSEMBLY AND SECURITY FEATURES

FIELD OF THE INVENTION

The present subject matter relates generally to temperature-controlled delivery boxes, and more particularly, to security and sanitization systems for temperature-controlled delivery boxes.

BACKGROUND OF THE INVENTION

Given the rise in food and grocery delivery services, temperature-controlled and access-secure delivery appliances are desirable to permit deliveries when the consumer is not home. For example, delivery appliances are typically positioned outdoors of a residence and have a climate control system for regulating the temperature within a storage container positioned within a cabinet of the delivery appliance. In this manner, the consumer may receive delivery of food orders and maintain that food at the desired storage temperature, even while not at home. For example, the user or the delivery service may set a temperature of the delivery appliance at a desired temperature to avoid spoiling perishable food items or to otherwise prevent degradation of the quality of the food which might otherwise occur if the food were stored in an uncontrolled environment.

Notably, conventional delivery appliances include no security systems or procedures, such that the systems are commonly the target of thieves or others who might obtain unauthorized access to the delivery items stored therein. In addition, items delivered into the delivery appliance may be contaminated with bacteria, viruses, and other contagious or unhealthy pathogens, and conventional delivery appliances include no manner of killing or otherwise neutralizing these pathogens.

Accordingly, a temperature-controlled delivery box and methods of controlling the same for improved operation would be desirable. More specifically, a temperature-controlled delivery box including systems for implementing sanitization and security procedures would be particularly beneficial.

BRIEF DESCRIPTION OF THE INVENTION

Aspects and advantages of the invention will be set forth in part in the following description, or may be apparent from the description, or may be learned through practice of the invention.

In one exemplary embodiment, a temperature-controlled delivery appliance is provided, including a cabinet, a storage container positioned within the cabinet for receiving delivered items for storage, a door rotatably mounted to the cabinet for providing selective access to the storage container, a sanitization assembly for selectively sanitizing the storage container or the delivered items, and a controller operably coupled to the sanitization assembly. The controller is configured to determine that a sanitization cycle is needed, determine that the door is closed, and perform the sanitization cycle in response to determining that the sanitization cycle is needed and the door is closed.

In another exemplary embodiment, a temperature-controlled delivery appliance is provided, including a cabinet, a storage container positioned within the cabinet for receiving delivered items for storage, a door rotatably mounted to the cabinet for providing selective access to the storage container, a locking mechanism for selectively locking the door in a closed position, and a controller operably coupled to the locking mechanism. The controller is configured to determine that an unlock condition has occurred and unlock the locking mechanism in response to determining that the unlock condition has occurred.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

Figure 1:
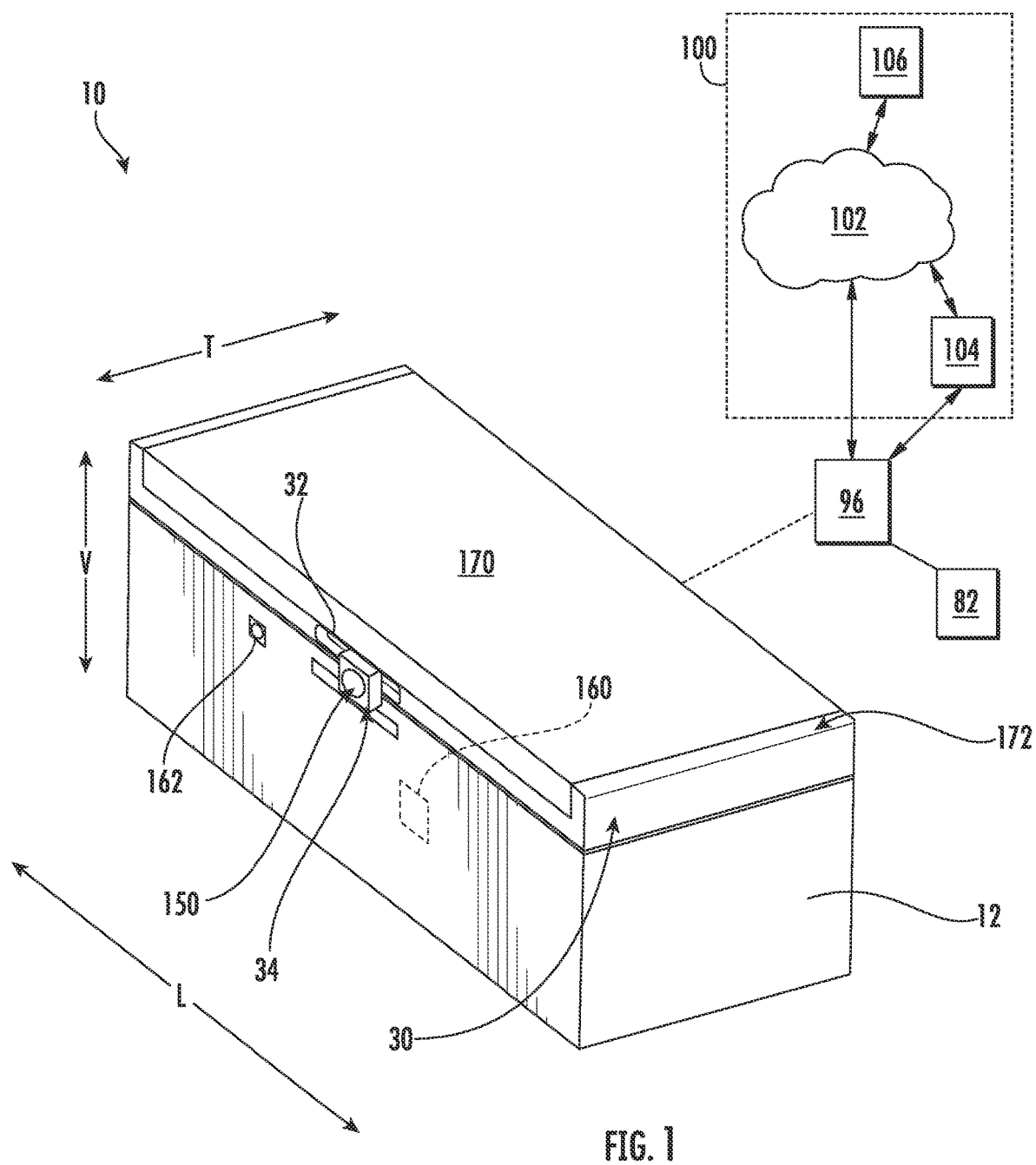
FIG. 1 is a front perspective view of a temperature-controlled delivery box according to an example embodiment of the present subject matter, with a door in a closed position.

Repeat use of reference characters in the present specification and drawings is intended to represent the same or analogous features or elements of the present invention.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

FIGS. 1 through 4 depict a temperature controlled delivery appliance 10 that is generally configured for receiving delivery of food items or other articles that are preferably stored in a temperature controlled environment. According to exemplary embodiments, temperature controlled delivery appliance 10 is positioned outside a consumer's residence and is configured for receiving grocery or other food deliveries. It should be appreciated that the term "temperature controlled delivery appliance," or simply "delivery appliance," is used in a generic sense herein to encompass any device intended for storing items in a refrigerated, heated, or other climate controlled and/or secure environment. In addition, it should be understood that the present subject matter is not limited to use in delivery appliances. Thus, the present subject matter may be used for any other suitable purpose, such as for receiving any other product or item that is desirably maintained in a temperature controlled environment or is otherwise stored in a secure manner.

In the illustrated example embodiment shown in FIG. 1, the temperature controlled delivery appliance 10 includes a casing or cabinet 12 that extends between a top and a bottom along a vertical direction V, between a first side and a second side along a lateral direction L, and between a front side and a rear side along a transverse direction T. Each of the vertical direction V, lateral direction L, and transverse direction T are mutually perpendicular to one another, such that an orthogonal coordinate system is generally defined.

As illustrated delivery appliance 10 includes one or more storage containers 14 mounted within cabinet 12. Specifically, according to the illustrated embodiment, delivery appliance 10 includes three storage containers 14 mounted in or suspended from a top panel 16 of cabinet 12, e.g., using any suitable support brackets, mechanical fasteners, welding, snap-fit mechanisms, etc. In addition, it should be appreciated that an insulating material (not shown), such as foam panels, fiberglass, or spray-in foam insulation, may be positioned within cabinet 12 around storage containers 14 to provide thermal and/or sound insulation to delivery appliance 10.

Figure 5:
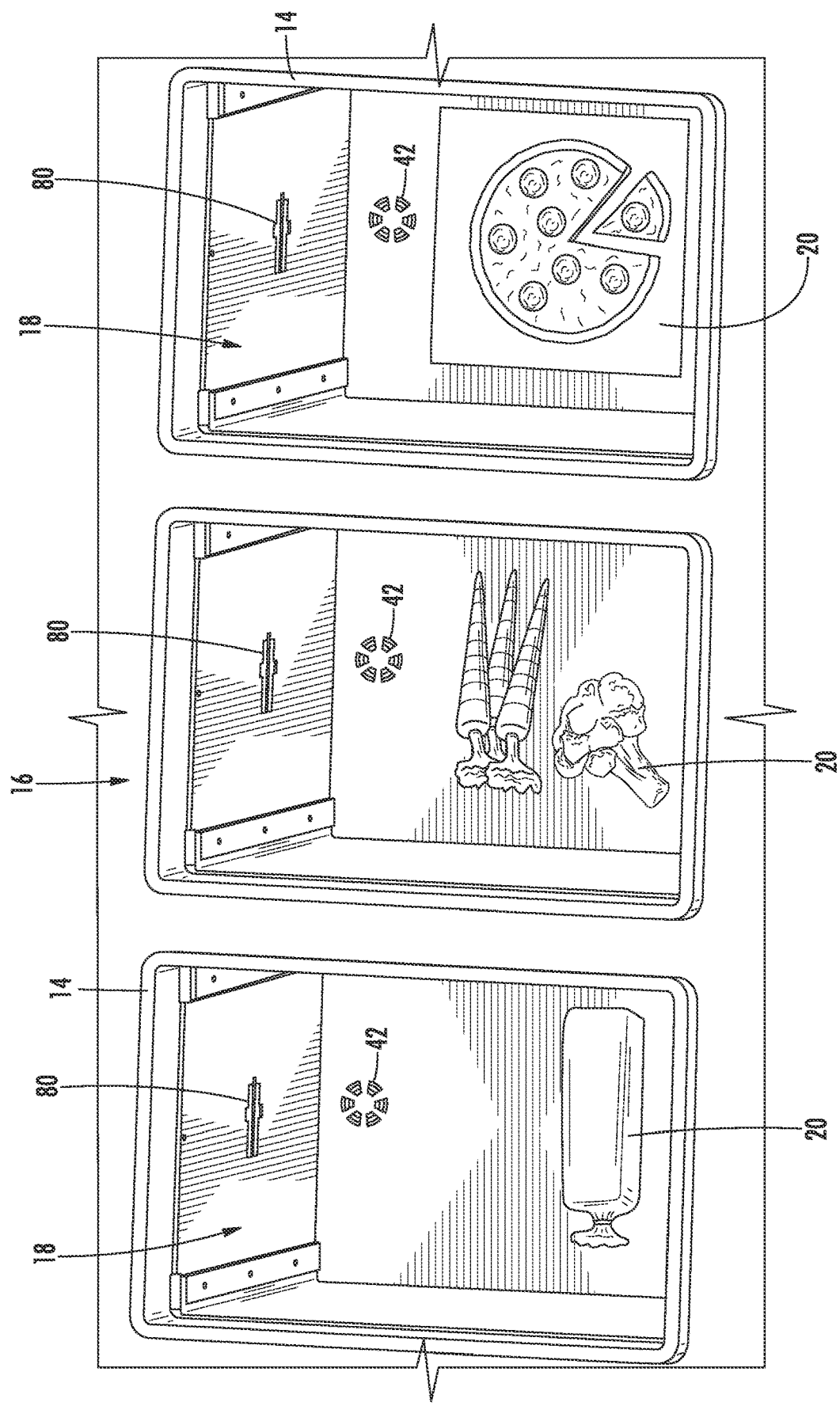
FIG. 5 provides a top view of storage containers positioned within the exemplary temperature-controlled delivery box of FIG. 1 according to an exemplary embodiment of the present subject matter.

As illustrated, each of the three storage containers 14 define an opening 18 at top panel 16 of cabinet 12. In this regard, food items 20 (FIG. 5) or other temperature controlled products may be positioned within storage containers 14 for temperature controlled storage, e.g., until they may be moved to a refrigerator appliance or pantry when the consumer returns home. As explained in detail below, each storage container 14 may be maintained at a different temperature for receiving foods that have different desired storage temperatures. For example, as illustrated in FIG. 5, storage containers 14 may have target temperatures suitable for storing room temperature food items 20 (such as bread, cereal, etc.), refrigerator food items (e.g., fruits, vegetables, milk, etc.), and frozen food items 20 (e.g., frozen pizza, ice cream, etc.).

Although the figures illustrate delivery appliance 10 as including three storage containers 14 having substantially rectangular cross sections and being spaced apart along the lateral direction L, it should be appreciated that the illustrated embodiment is used only as an example. According to alternative embodiments, delivery appliance 10 may include any suitable number of storage containers 14 having any suitable shape, size, and configuration. In addition, aspects of the present subject matter may apply to conventional refrigerator appliance with doors pivotally mounted to a front of the appliance. Such embodiments are contemplated as within the scope of the present subject matter.

Delivery appliance 10 further includes a door 30 rotatably attached to cabinet 12 in order to permit selective access to storage containers 14. Specifically, as illustrated, door 30 is pivotally mounted to a back of cabinet 12 and is positioned over openings 18 in the closed position. A handle 32 is mounted to or defined in door 30 to assist a user with opening and closing door 30 and a latch assembly 34 is mounted to cabinet 12 and/or door 30 for selectively locking door 30 in the closed position. Latch assembly 34 may be desirable, for example, to ensure only secured access (e.g., via the consumer or delivery person) and to prevent tampering or theft after food items 20 are delivered. According to the illustrated embodiment, delivery appliance 10 includes a single door 30 that permits or prevents access to each storage container 14. However, it should be appreciated that according to alternative embodiments, delivery appliance 10 may include any suitable number, type, and configuration of doors 30. For example, delivery appliance 10 may include three doors 30, each of which provides access to one of the storage containers 14. Moreover, it should be appreciated that one or more latch assemblies 34 may be used, and each of these latch assemblies 34 may require a code or keyword to be entered to prevent locking during dangerous conditions, e.g., for child safety.

Delivery appliance 10 may include any suitable mounting base, legs, or other suitable support structure. For example, according to the illustrated embodiment, delivery appliance 10 is supported by rotating casters 36 that are mounted at each of the four corners of cabinet 12. In this manner, delivery appliance 10 may be easily moved or transported as desired. According to alternative embodiments, delivery appliance may have stationary support feet, sliding support feet, or any other suitable supporting device or mechanism.

Figure 4:
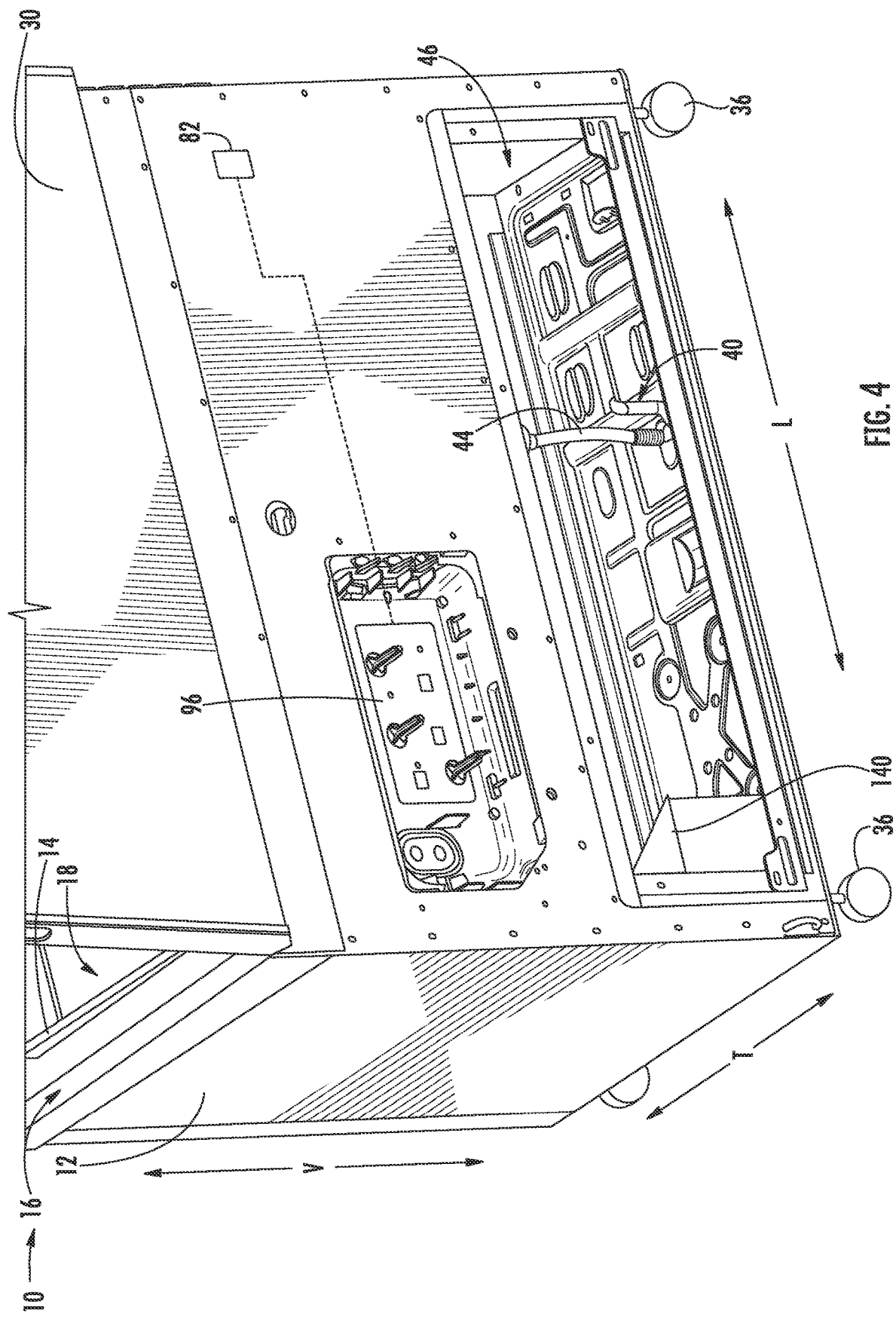
FIG. 4 is a rear perspective view of the exemplary temperature-controlled delivery box of FIG. 1, with a back cover removed to reveal a controls compartment and a mechanical compartment.
Figure 6:
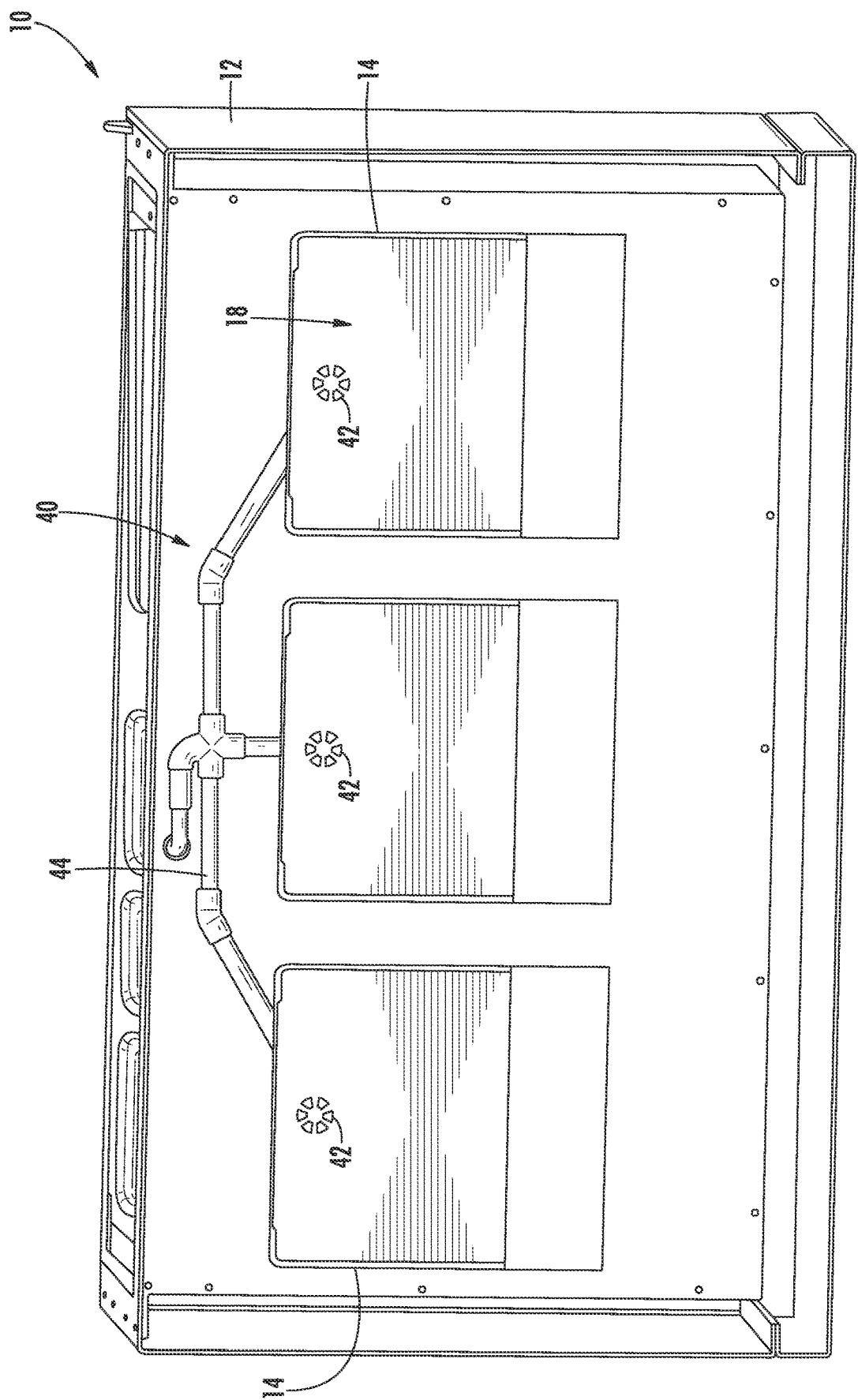
FIG. 6 provides a top view of storage containers positioned within the exemplary temperature-controlled delivery box of FIG. 1, with a top panel removed to reveal a drainage system according to an exemplary embodiment of the present subject matter.

Referring now generally to FIGS. 4 through 6, delivery appliance 10 further includes a drainage system 40 for collecting and discharging liquids from within storage containers 14, e.g., such as melted items, condensation, melted frost, etc. Specifically, a drain 42 is defined in a bottom of each storage container 14. Drain 42 may be in fluid communication with one or more drainage pipes 44 for routing liquid out of storage containers 14 under the force of gravity. The drainage pipes 44 may merge and pass all collected liquid through a mechanical compartment 46 (FIG. 4) where it may be discharged from delivery appliance 10 (e.g., to an external drain) or used for other purposes within delivery appliance 10. Although drainage system 40 is illustrated as a gravity operated system, it should be appreciated that a suitable drainage pump may be used according to alternative embodiments. Moreover, it should be appreciated that according to exemplary embodiments, delivery appliance 10 may include no drainage system or a drainage system having another suitable configuration.

Figure 7:
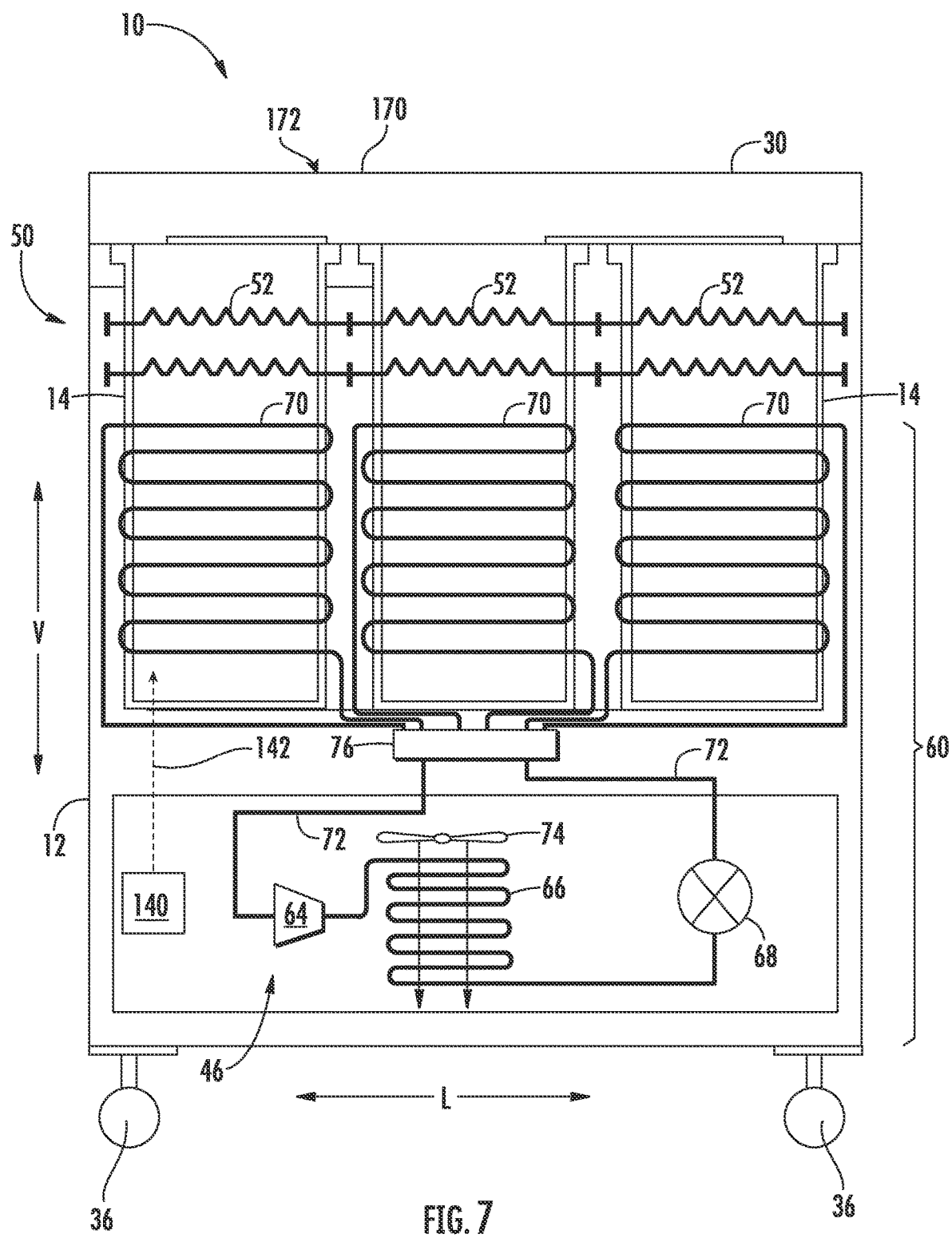
FIG. 7 provides a schematic view of a sealed cooling system configured for cooling the exemplary temperature-controlled delivery box of FIG. 1 according to an exemplary embodiment of the present subject matter.

Referring now specifically to FIGS. 4 and 7, mechanical compartment 46 may be defined in a rear wall of cabinet 12 and may be configured for receiving various operating components of delivery appliance 10. For example, delivery appliance 10 may include a climate control system 50 that includes various components for regulating one or more container temperatures, e.g., the temperature measured within respective storage containers 14. Thus, climate control system 50 may generally be in thermal communication with storage containers 14 and some or all components of climate control system 50 may be mounted within mechanical compartment 46.

Referring now specifically to FIG. 7, a schematic view of certain components of temperature controlled delivery appliance 10 and climate control system 50 will be illustrated and described according to an exemplary embodiment. As described below, climate control system 50 may generally include a system or devices for heating storage containers 14 and/or a system or devices for cooling storage containers 14. Although an exemplary climate control system 50 is described below, it should be appreciated that climate control system 50 may include different component, configuration, and subsystems for heating, cooling, humidifying, dehumidifying, or otherwise controlling the climate with each of the respective storage containers 14.

According to exemplary embodiments, it may sometimes be desirable to raise the container temperature within one or more storage containers 14, e.g., when it is very cold outside or if hot food items 20 are being stored. In such cases, delivery appliance 10 may include a heating device 52 in thermal communication with one or more storage containers 14 for regulating the temperature of the storage containers 14. Thus, heating device 52 may be selectively activated and deactivated to control the container temperature. In general, heating device 52 may be any suitable type of heating element, such as an electric resistance heating element. In addition, heating device 52 may be used periodically to melt any frost build-up within storage containers 14.

In addition, it may frequently be desirable to lower the container temperature of one or more storage containers 14, e.g., when is it relatively warm outside or when chilled or perishable food items 20 are stored. In this regard, delivery appliance 10 may include features to operate delivery appliance as a refrigerator and/or freezer appliance. For example, delivery appliance 10 may include a sealed refrigeration system or sealed system 60, which is generally configured for executing a vapor compression cycle for cooling storage containers 14, as explained below.

In this regard, for example, sealed system 60 may include a compressor 64, a condenser 66, an expansion device 68, and one or more evaporators 70 connected in series by fluid conduit 72 that is charged with a refrigerant. As will be understood by those skilled in the art, sealed system 60 may include additional components, e.g., at least one additional evaporator, compressor, expansion device, and/or condenser. As an example, sealed system 60 may include three evaporators wrapped directly around storage containers 14. Moreover, it should be appreciated that according to alternative embodiments, one or more evaporators 70 may be connected in parallel and sealed system 60 may include one or more switching valves (e.g., similar to refrigerant control valve 76, described below) for regulating the flow of refrigerant and associated cooling capacity.

Within sealed system 60, refrigerant flows into compressor 64, which operates to increase the pressure of the refrigerant. This compression of the refrigerant raises its temperature, which is lowered by passing the refrigerant through condenser 66. Within condenser 66, heat exchange with ambient air takes place so as to cool the refrigerant. A fan 74 may be used to pull air across condenser 66, as illustrated by arrows in FIG. 7, so as to provide forced convection for a more rapid and efficient heat exchange between the refrigerant within condenser 66 and the ambient air. Thus, as will be understood by those skilled in the art, increasing air flow across condenser 66 can, e.g., increase the efficiency of condenser 66 by improving cooling of the refrigerant contained therein.

An expansion device 68 (e.g., a electronic expansion valve, capillary tube, or other restriction device) receives refrigerant from condenser 66. From expansion device 68, the refrigerant enters evaporator 70. Upon exiting expansion device 68 and entering evaporator 70, the refrigerant drops in pressure. Due to the pressure drop and/or phase change of the refrigerant, evaporator 70 is cool relative to storage containers 14 of delivery appliance 10. As such, by wrapping evaporators 70 around storage containers 14 or positioning evaporator 70 coils within the walls of the storage containers 14, the temperature within storage containers 14 may be lowered.

Notably, as illustrated in FIG. 7, delivery appliance 10 may include three storage containers 14, each of which may have a dedicated evaporator 70. According to an exemplary embodiment, a single compressor 64, condenser 66, and expansion device 68 may support the operation of such evaporators 70. In this regard, sealed system 60 may include a refrigerant control valve 76 for regulating the flow of refrigerant to evaporators 70 to provide selective and independent cooling of each storage container 14. In this manner, using climate control system 50, each storage container 14 may have a different pre-conditioning temperature or target temperature, as described in more detail below. It should be appreciated that more or fewer storage containers 14 may be used and the configuration of one or more evaporators 70 may vary while remaining within the scope of the present subject matter.

The sealed system 60 depicted in FIG. 7 is provided by way of example only. Thus, it is within the scope of the present subject matter for other configurations of the refrigeration system to be used as well. For example, according to alternative embodiments, cooled air may be passed over evaporator 70 and into storage containers 14 instead of relying on contact cooling. In addition, although sealed system 60 is described above as performing a vapor compression cycle to refrigerate storage containers 14, it should be appreciated that a sealed system may be alternately operated as a heat pump, e.g., and thus perform a heat pump cycle for heating storage containers 14. In this regard, for example, sealed system 60 may include a four-way reversing valve which could also be used to reverse the flow of refrigerant within fluid conduit 72 such that condenser 66 operates as an evaporator, and evaporator 70 operates as a condenser.

In some embodiments, delivery appliance 10 also includes one or more sensors that may be used to facilitate improved operation of delivery appliance 10, such as described below. For example, in order to obtain temperature or humidity data, delivery appliance 10 may include a plurality of temperature sensors and/or humidity sensors. Specifically, as shown in FIG. 5, a container temperature sensor 80 may be positioned within or placed in thermal communication with each storage container 14 for measuring a container temperature therein. For example, according to the illustrated embodiment, container temperature sensors 80 are mounted to a rear wall of each storage container 14. Alternatively, container temperature sensors 80 may be positioned at any other suitable location proximate to storage containers 14 for providing data indicative of the container temperature. In addition, an ambient temperature sensor 82 may be positioned outside cabinet 12 for measuring a temperature of the environment in which delivery device 10 is located.

As used herein, "temperature sensor" or the equivalent is intended to refer to any suitable type of temperature measuring system or device positioned at any suitable location for measuring the desired temperature. Thus, for example, temperature sensors 80, 82 may each be any suitable type of temperature sensor, such as a thermistor, a thermocouple, a resistance temperature detector, etc. In addition, temperature sensors 80, 82 may be positioned at any suitable location and may output a signal, such as a voltage, to a controller that is proportional to and/or indicative of the temperature within storage container 14 or the ambient environment, respectively. Although exemplary positioning of temperature sensors is described herein, it should be appreciated that delivery appliance 10 may include any other suitable number, type, and position of temperature, humidity, and/or other sensors according to alternative embodiments.

Referring again to FIG. 3, delivery appliance 10 may include a control panel 90 including one or more selector inputs 92, such as knobs, buttons, touchscreen interfaces, etc. Additionally, a display 94, such as an indicator light or a screen, may be provided on control panel 90. Control panel 90, selector inputs 92, and display 94 may be in communication with a processing device or controller 96. In this manner, controller 96 may receive control inputs from selector inputs 92, may display information using display 94, and may otherwise regulate operation of the appliance. For example, signals generated in controller 96 may operate delivery appliance 10, including climate control system 50 and other system components, in response to the position of selector inputs 92 and other control commands.

Figure 8:
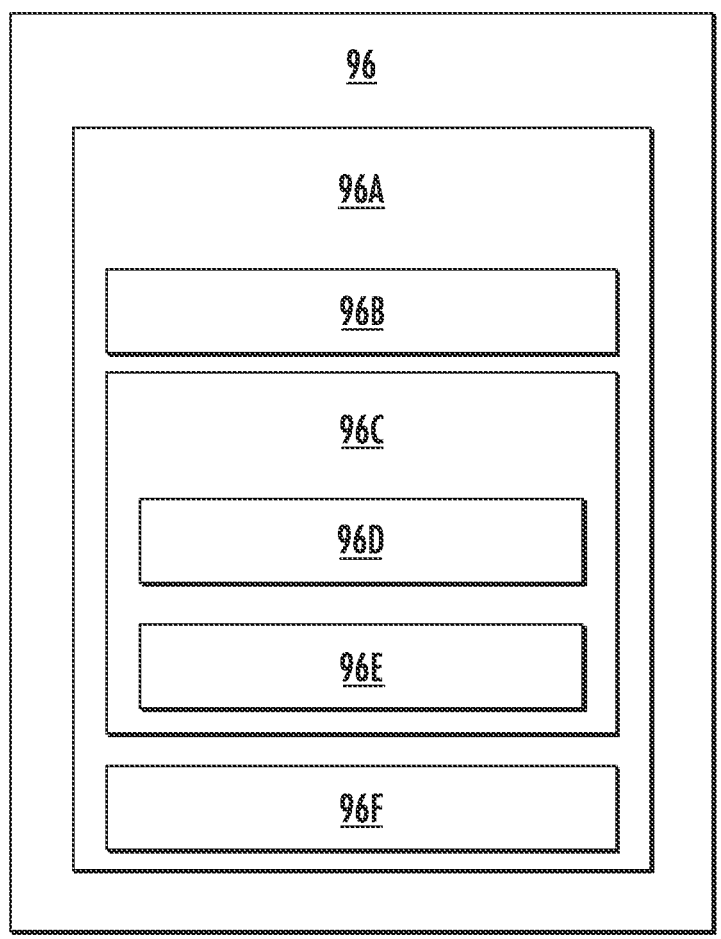
FIG. 8 depicts certain components of a controller according to example embodiments of the present subject matter.

FIG. 8 depicts certain components of controller 96 according to example embodiments of the present disclosure. Controller 96 can include one or more computing device(s) 96A which may be used to implement methods as described herein. Computing device(s) 96A can include one or more processor(s) 96B and one or more memory device(s) 96C. The one or more processor(s) 96B can include any suitable processing device, such as a microprocessor, microcontroller, integrated circuit, an application specific integrated circuit (ASIC), a digital signal processor (DSP), a field-programmable gate array (FPGA), logic device, one or more central processing units (CPUs), graphics processing units (GPUs) (e.g., dedicated to efficiently rendering images), processing units performing other specialized calculations, etc. The memory device(s) 96C can include one or more non-transitory computer-readable storage medium(s), such as RAM, ROM, EEPROM, EPROM, flash memory devices, magnetic disks, etc., and/or combinations thereof.

The memory device(s) 96C can include one or more computer-readable media and can store information accessible by the one or more processor(s) 96B, including instructions 96D that can be executed by the one or more processor(s) 96B. For instance, the memory device(s) 96C can store instructions 96D for running one or more software applications, displaying a user interface, receiving user input, processing user input, etc. In some implementations, the instructions 96D can be executed by the one or more processor(s) 96B to cause the one or more processor(s) 96B to perform operations, e.g., such as one or more portions of methods described herein. The instructions 96D can be software written in any suitable programming language or can be implemented in hardware. Additionally, and/or alternatively, the instructions 96D can be executed in logically and/or virtually separate threads on processor(s) 96B.

The one or more memory device(s) 96C can also store data 96E that can be retrieved, manipulated, created, or stored by the one or more processor(s) 96B. The data 96E can include, for instance, data to facilitate performance of methods described herein. The data 96E can be stored in one or more database(s). The one or more database(s) can be connected to controller 96 by a high bandwidth LAN or WAN, or can also be connected to controller through network(s) (such as network 102 described below). The one or more database(s) can be split up so that they are located in multiple locales. In some implementations, the data 96E can be received from another device.

The computing device(s) 96A can also include a communication module or interface 96F used to communicate with one or more other component(s) of controller 96 or delivery appliance 10 over the network(s). The communication interface 96F can include any suitable components for interfacing with one or more network(s), including for example, transmitters, receivers, ports, controllers, antennas, or other suitable components.

As illustrated and described in FIG. 8, controller 96 includes a memory and microprocessor, such as a general or special purpose microprocessor operable to execute programming instructions or micro-control code associated with methods described herein. However, it should be appreciated that according to alternative embodiments, controller 96 may be constructed without using a microprocessor, e.g., using a combination of discrete analog and/or digital logic circuitry (such as switches, amplifiers, integrators, comparators, flip-flops, AND gates, and the like) to perform control functionality instead of relying upon software. Selector inputs 92, display 94, sensors, and other components of delivery appliance 10 may be in communication with controller 96 via one or more signal lines or shared communication busses.

Referring again to FIG. 1, a schematic diagram of an external communication system 100 will be described according to an exemplary embodiment of the present subject matter. In general, external communication system 100 is configured for permitting a consumer, a grocery delivery service, or another entity to communicate with and/or control delivery appliance 10, e.g., through controller 96. For example, this communication may be used to provide and receive delivery notifications or instructions, as described below. Alternatively, such notifications and information may be input directly through control panel 90.

As illustrated, external communication system 100 permits controller 96 of delivery appliance 10 to communicate with external devices either directly or through a network 102. For example, a consumer may use a consumer device 104 to communicate directly with delivery appliance 10. For example, consumer devices 104 may be in direct or indirect communication with delivery appliance 10, e.g., directly through a local area network (LAN), Wi-Fi, Bluetooth, Zigbee, etc. or indirectly through network 102. In general, consumer device 104 may be any suitable device for providing and/or receiving communications or commands from a user. In this regard, consumer device 104 may include, for example, a personal phone, a tablet, a laptop computer, or another mobile device.

In addition, a remote server 106 may be in communication with delivery appliance 10 and/or consumer device 104 through network 102. In this regard, for example, remote server 106 may facilitate or operate a grocery delivery service. In this regard, remote server 106 may be a cloud-based server 106, and is thus located at a distant location, such as in a separate state, country, etc. In general, communication between the remote server 106 and the client devices may be carried via a network interface using any type of wireless connection, using a variety of communication protocols (e.g. TCP/IP, HTTP, SMTP, FTP), encodings or formats (e.g. HTML, XML), and/or protection schemes (e.g. VPN, secure HTTP, SSL).

In general, network 102 can be any type of communication network. For example, network 102 can include one or more of a wireless network, a wired network, a personal area network, a local area network, a wide area network, the internet, a cellular network, etc. According to an exemplary embodiment, consumer device 104 may communicate with a remote server 106 over network 102, such as the internet, to place food orders, process payments, etc. In addition, consumer device 104 and remote server 106 may communicate with delivery appliance 10 to coordinate the delivery and receipt of food items 20, as described in detail below.

External communication system 100 is described herein according to an exemplary embodiment of the present subject matter. However, it should be appreciated that the exemplary functions and configurations of external communication system 100 provided herein are used only as examples to facilitate description of aspects of the present subject matter. System configurations may vary, other communication devices may be used to communicate directly or indirectly with one or more delivery appliances, other communication protocols and steps may be implemented, etc. These variations and modifications are contemplated as within the scope of the present subject matter.

Referring still generally to FIGS. 1 through 7, delivery appliance 10 may further include a sanitization assembly 120 that is generally configured for selectively sanitizing one or more storage containers 14 and/or food items 20 positioned within storage containers 14. Although exemplary sanitization assemblies 120 are described herein, it should be appreciated that delivery appliance 10 may include any suitable number, type, and configuration of sanitization assemblies for facilitating improved sanitization, e.g., by killing bacteria, viruses, pathogens, etc. Variations and modifications to sanitization assembly 120 may be made while remaining within the scope of the present subject matter.

Figure 2:
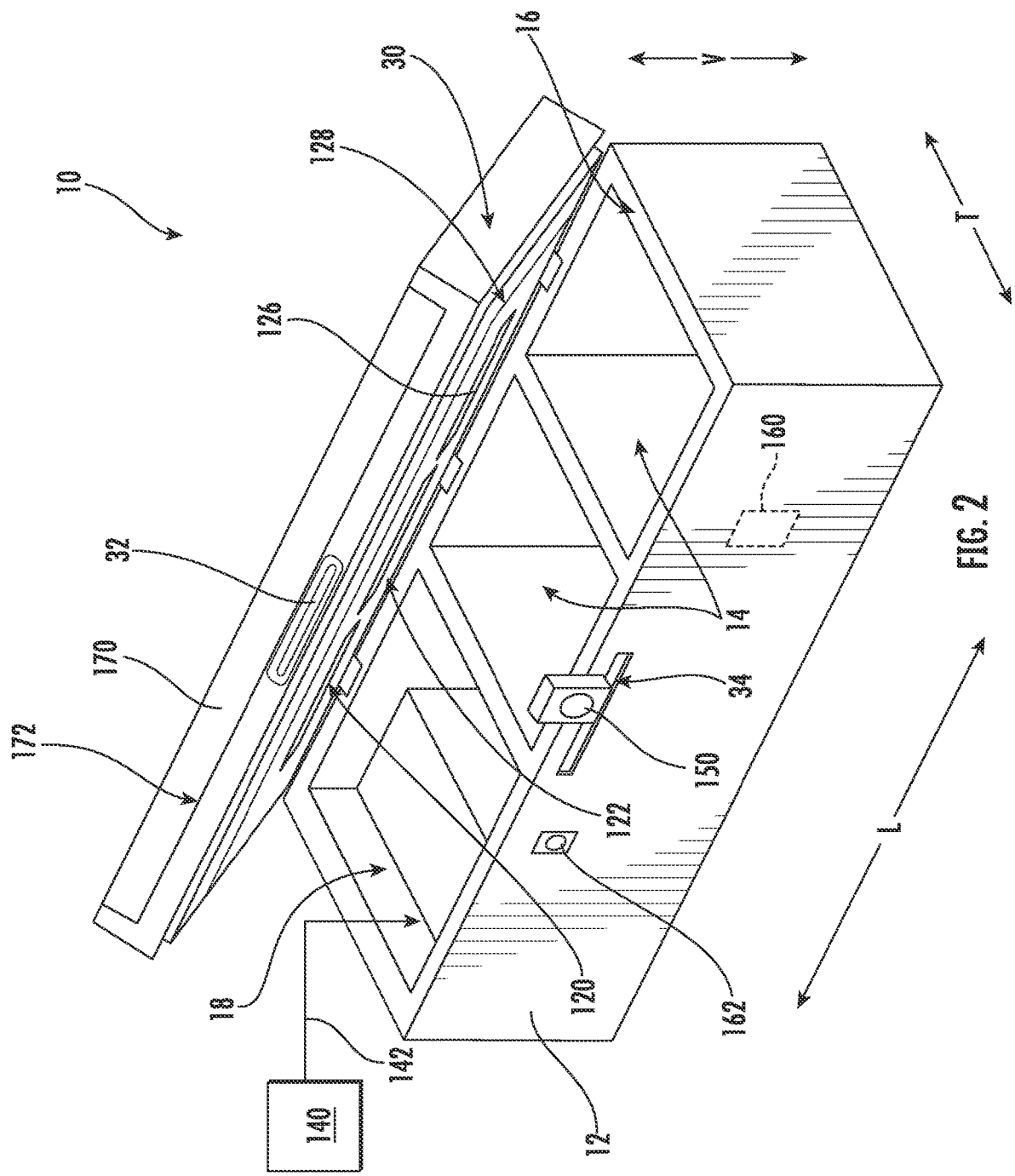
FIG. 2 is a front perspective view of the exemplary temperature-controlled delivery box of FIG. 1 according to an example embodiment of the present subject matter, with the door in an open position.
Figure 3:
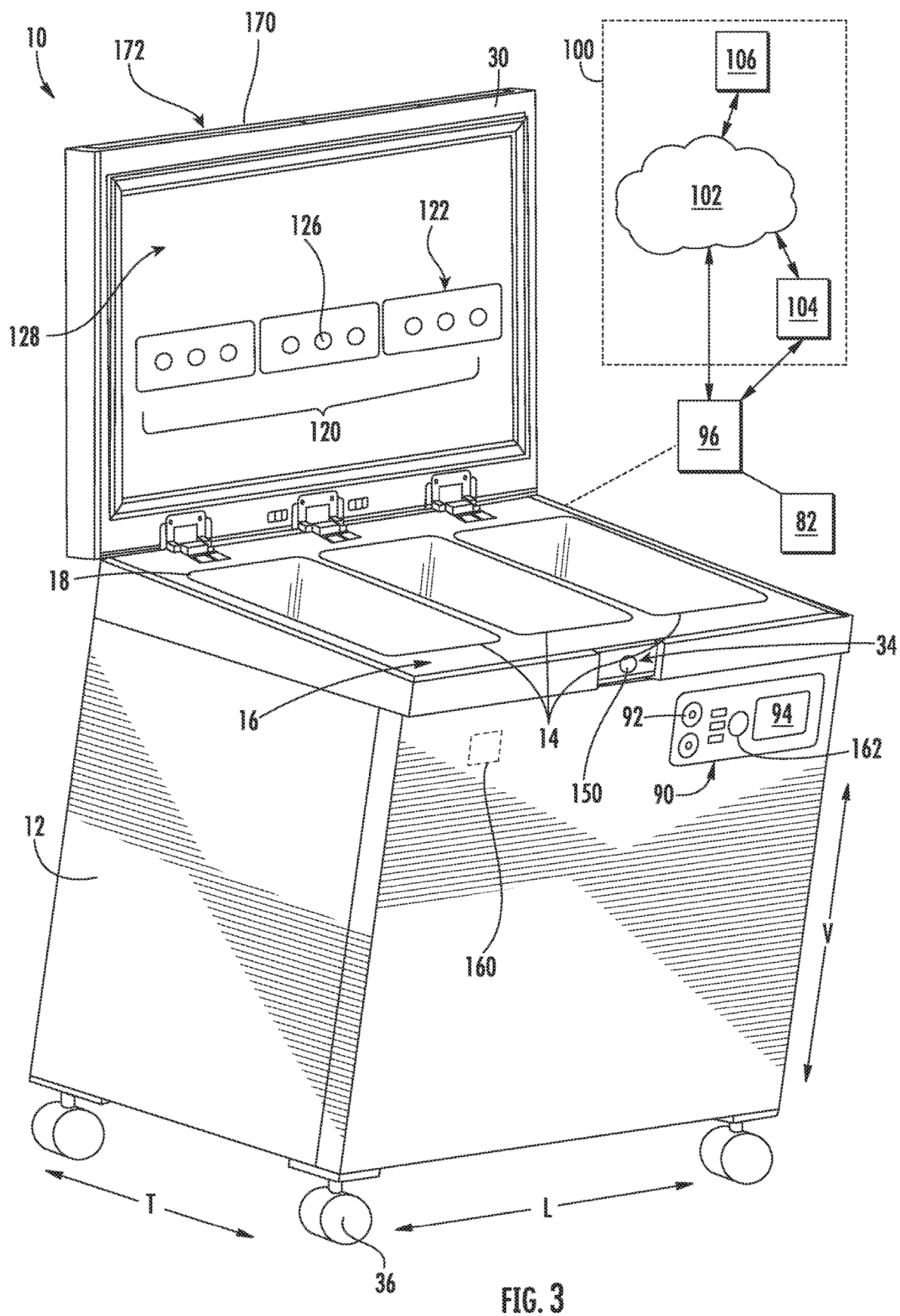
FIG. 3 is another front perspective view of the exemplary temperature-controlled delivery box of FIG. 1 according to an example embodiment of the present subject matter, with the door in an open position.
Figure 9:
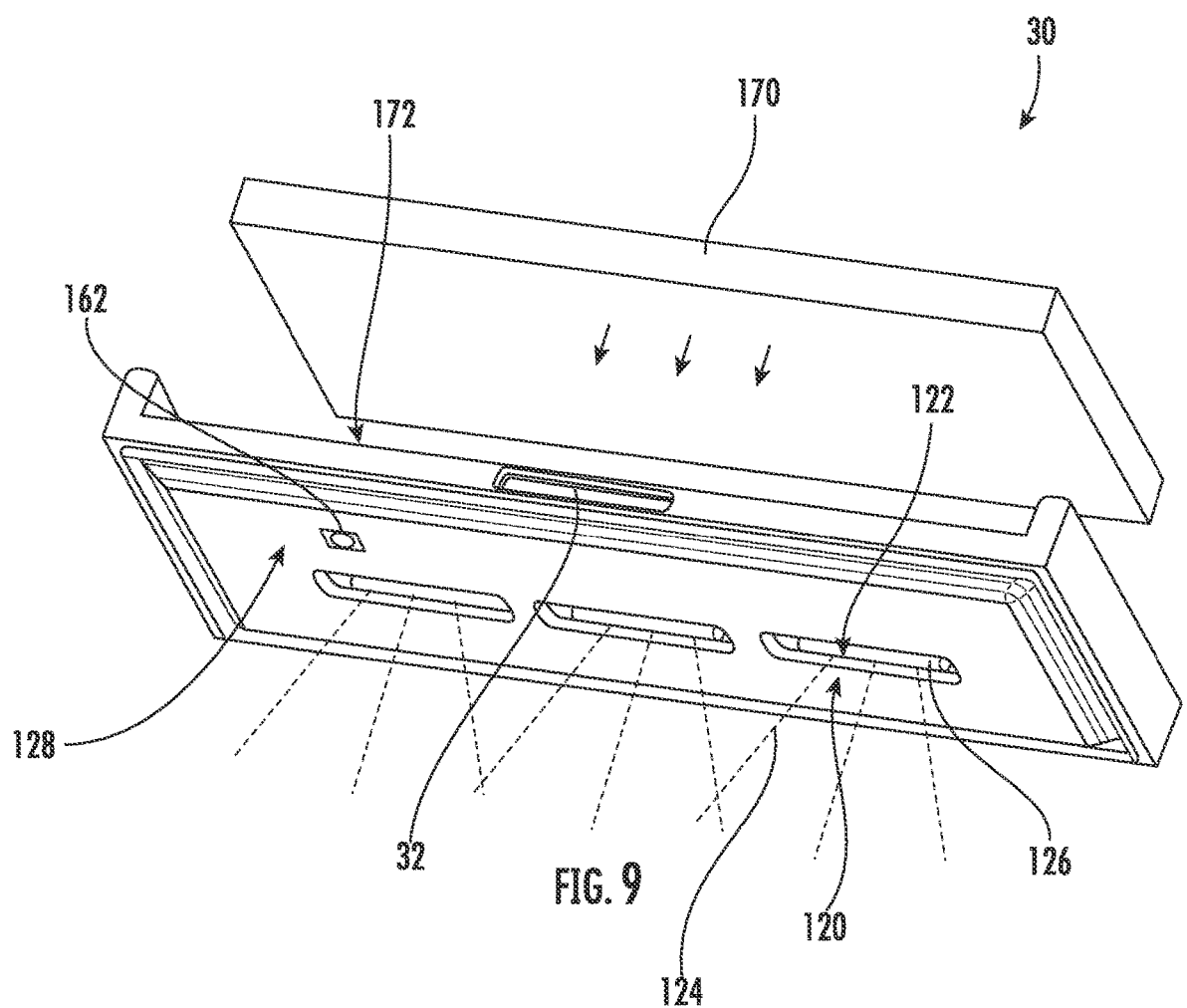
FIG. 9 provides a bottom perspective view of a door and sanitizing light assembly of the exemplary temperature-controlled delivery box of FIG. 1 according to an exemplary embodiment of the present subject matter.

For example, as best shown in FIGS. 2, 3, and 9, sanitization assembly 120 may include a sanitizing light assembly 122 is configured for illuminating storage containers 14 with sanitizing light (e.g. as identified generally by reference numeral 124). In this regard, sanitizing light assembly 122 may include any suitable number, type, and configuration of light sources 126 for generating sanitizing light 124. According to the exemplary illustrated embodiment, sanitizing light assembly 122 includes three light sources 126, with one light source positioned over each storage container 14. More particularly, these light sources 126 are positioned on a bottom surface 128 of door 30, such that closing door 30 places light sources 126 over each respective storage container 14. In this manner, sanitizing light assembly 122 may selectively activate light sources 126 in the desired storage containers 14 to facilitate a sanitization process.

It should be appreciated that light sources 126 may be any type of light sources that generates sanitizing light 124. For example, according to exemplary embodiments, light sources 126 are ultraviolet (UV) lights. Indeed, according to the illustrated exemplary embodiment, light sources 126 are C-band ultraviolet lights, i.e., UV-C light. According to exemplary embodiments, light sources 126 may generate ultraviolet light having a wavelength of between 50 and 500 nanometers, between 100 and 400 nanometers, between 150 and 300 nanometers, or between about 100 and 280 nanometers. In addition, it should be appreciated that light sources 126 may include different types of lights producing a broad spectrum of sanitizing light 124 as needed for a given application.

In addition, or alternatively, sanitization assembly 120 may include an ozone gas generator 140 is generally configured for generating ozone gas (e.g., as identified generally by reference numeral 142) within one or more storage containers 14. It should be appreciated that ozone gas generator 140 may further include a distribution system, such as a system of distribution ducts for selectively filling each respective storage container 14 with the desired amount or concentration of ozone gas 142. It should be appreciated that sanitizing light 124 and ozone gas 142 may be used together or interchangeably as needed to sanitize storage containers 14.

Notably, it may commonly be desirable to prevent a user access to storage containers 14 when a sanitization processes being performed or at other times where restricted access is desirable. Accordingly, delivery appliance 10 may include a locking mechanism 150 for selectively locking door 30 in the closed position. For example, according to the illustrated embodiment, locking mechanism 150 may be a part of or replace latch assembly 34. In addition, according to exemplary embodiments, locking mechanism 150 may be in operative communication with controller 96 such that controller 96 may make informed decisions on when to actuate locking mechanism 150 and lock the door 30, e.g., such as during a sanitization cycle using sanitizing light assembly 122 or ozone gas generator 140.

According to exemplary embodiments, controller 96 may automatically lock door 30 during a sanitization cycle, e.g., to prevent user access and exposure to sanitizing light 124 and/or ozone gas 142. In this regard, for example, controller 96 may be configured to determine a sanitization station cycle is needed, determine that the door is closed, and perform the sanitization cycle in response to determining that the sanitization cycle is needed and the door is closed. In this regard, controller 96 may prevent the initiation of a sanitization cycle if door 30 is not closed. Moreover, controller 96 may be configured for immediately stopping the sanitization cycle if door 30 is opened during a sanitization cycle.

Notably, controller 96 may be programmed to determine that a sanitization cycle is needed in a variety of situations. For example, according to an exemplary embodiment, controller 96 may determine that a sanitization cycle is needed after a predetermined period of time has passed. Thus, for example, controller 96 may be programmed to perform a sanitization cycle every two hours, every 12 hours, every day, or at any other suitable interval. According to still other embodiments, controller 96 may be programmed to perform the sanitization cycle immediately after food items 20 are delivered. In this regard, controller 96 may be configured to determine that a delivery has occurred and perform a sanitization cycle immediately after delivery occurs and door 30 is closed. Alternatively, a consumer may choose when to run a sanitization cycle and/or may be prompted to authorize the locking of the door and the commencement of a sanitization cycle, e.g., after being provided with images from camera 162. In addition, controller 96 may be programmed for actuating locking mechanism 150 prior to any sanitization cycle.

According to exemplary embodiments, locking mechanism 150 may remain locked to prevent door 30 from being opened until an unlock condition or event has occurred. In this regard, controller 96 may maintain locking mechanism 150 in the locked position until it determines that an unlock condition has occurred, at which point controller 96 could unlock the locking mechanism 150. As used herein, the term "unlock condition" may be used to refer to any external stimulus or input received by controller 96 that corresponds to a condition where the door 30 may be opened. In this regard, for example, the unlock condition may be based on a keypad entry, e.g., such as when a user inputs an appropriate security key using selector inputs 92. According still other embodiments, the unlock condition may be based on a user input from a remote device, such as consumer device 104. It should be appreciated that other suitable unlock conditions are possible and within the scope of the present subject matter.

According to exemplary embodiments, delivery appliance 10 may include other suitable security and user accessibility features. In this regard, according to an exemplary embodiment, controller 96 may be configured for providing an alert when delivery appliance 10 is moved outside of the wireless communication network of the consumer's residence. In this regard, a wireless communication module (e.g., such as communication module 96F) may be in communication with a Wi-Fi network (e.g., such as network 102) at the consumer's residence. When the wireless signal from network 102 becomes weak or slowly dissipates, controller 96 may conclude that the cabinet 12 has been moved out of range of wireless network 102 and may provide a user notification, e.g., via remote device 104. Alternatively, controller 96 may be programmed to provide a security alert, such as initiating a call to emergency services, setting off the alarm, etc.

According still other embodiments, delivery appliance 10 may include a motion sensor 160 that is generally configured for detecting when cabinet 12 has been moved. In this regard, if someone attempts to steal delivery appliance 10, a motion sensor 160 may trigger controller 96 to provide a user notification or security alert. According still other embodiments, delivery appliance 10 may include a camera 162 mounted to cabinet 12 for obtaining an image of a user or delivery person interacting with delivery appliance 10. In this regard, when a delivery of food items 20 occurs, controller 96 may be configured for taking an image of the delivery or the items food items 20 being positioned within the storage containers 14. Controller 96 may further transmit this image or video to a user, e.g., via remote device.

According to the illustrated embodiment, camera 162 is positioned on a front of cabinet 12 to monitor external interactions with delivery appliance. However, it should be appreciated that delivery appliance 10 may include one or more cameras positioned at any other suitable locations in or around delivery appliance 10. In this regard, for example, delivery appliance 10 may include a camera 162 that placed in a bottom side of door 30 (such as shown in FIG. 9) such that it is facing a person accessing the storage containers 14 when door 30 is open. In addition, the same camera may provide for monitoring of food items 20 or other objects within storage container 14 when door 30 is closed. In this regard, delivery appliance 10 may activate a light source that is integral with camera 162 or may activate sanitizing light assembly 122 such that camera 162 may obtain images from within storage container 14 and objects positioned therein when the door is closed. Notably, such a camera 162 could facilitate improved safety methods, e.g., by monitoring for moving object or detecting for children before locking door 30 using latch assembly 34.

Notably, delivery appliance 10 may include other features that are particularly suitable or aesthetically pleasing to a user. In this regard, for example, delivery appliance 10 may be appropriately sized and designed such that it is concealed or disguised as another object, e.g., such as another object commonly found on a front porch or other location where delivery appliance 10 is installed. For example, delivery appliance 10 may be disguised as a flowerpot or a seating bench. In this regard, for example, temperature control delivery appliance 10 may include a seating area 170 defined on or positioned on top of cabinet 12. For example, according to the illustrated embodiment, a top surface 172 of door 30 may define a profiled seating area 170. Therefore, when a user closes door 30, the seating area 170 is positioned for use.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A temperature-controlled delivery appliance comprising:
   a cabinet;
   a storage container positioned within the cabinet for receiving delivered items for storage;
   a door rotatably mounted to the cabinet for providing selective access to the storage container;
   a locking mechanism for selectively locking the door in the closed position;
   a sanitization assembly for selectively sanitizing the storage container or the delivered items; and
   a controller operably coupled to the sanitization assembly, the controller being configured to:
      determine that a sanitization cycle is needed;
      determine that the door is closed;
      lock the door using the locking mechanism prior to performing the sanitization cycle; and
      perform the sanitization cycle in response to determining that the sanitization cycle is needed and the door is closed.

2. The temperature-controlled delivery appliance of claim 1, wherein the sanitization assembly is a sanitizing light assembly configured for illuminating the storage container with sanitizing light.

3. The temperature-controlled delivery appliance of claim 2, wherein the sanitizing light assembly is mounted on a bottom of the door.

4. The temperature-controlled delivery appliance of claim 2, wherein the sanitizing light assembly comprises:
   an ultraviolet light.

5. The temperature-controlled delivery appliance of claim 4, wherein the ultraviolet light is UV-C light having a wavelength of between 100 nanometers and 280 nanometers.

6. The temperature-controlled delivery appliance of claim 1, wherein the sanitization assembly comprises:
   an ozone generator for selectively generating and distributing an ozone gas within the storage container.

7. The temperature-controlled delivery appliance of claim 1, wherein the controller is configured to:
   determine that a delivery has occurred; and
   perform a sanitization cycle immediately after the delivery occurs using the sanitization assembly.

8. The temperature-controlled delivery appliance of claim 1 wherein the controller is further configured to:
   determine that an unlock condition has occurred; and
   unlock the locking mechanism in response to determining that the unlock condition has occurred.

9. The temperature-controlled delivery appliance of claim 8, wherein the unlock condition is based on a keypad entry.

10. The temperature-controlled delivery appliance of claim 8, wherein the unlock condition is based on a user input from a remote device.

11. The temperature-controlled delivery appliance of claim 1, further comprising:
   a wireless communication module in communication with a wireless network, wherein the controller is operably coupled to the wireless communication module and is configured to:
   determine that the cabinet has been moved out of range of the wireless network; and
   provide a user notification or security alert.

12. The temperature-controlled delivery appliance of claim 11, further comprising:
   a motion sensor for detecting when the cabinet is being moved, wherein the user notification is provided when the motion sensor detects movement.

13. The temperature-controlled delivery appliance of claim 1, further comprising:
   a seating area mounted on a top of the cabinet.

14. The temperature-controlled delivery appliance of claim 1, wherein the door is mounted to a top of the cabinet, and wherein a seating area is defined on a top surface of the door in a closed position.

15. The temperature-controlled delivery appliance of claim 1, wherein the temperature-controlled delivery appliance further comprises:
   a camera mounted to the cabinet or a lid for obtaining an image of a user of the appliance or of the storage container.

16. The temperature-controlled delivery appliance of claim 1, further comprising:
   a climate control system in thermal communication with the storage container for regulating a temperature of the storage container, wherein the controller is operably coupled to the climate control system, the controller being configured to:
   obtain a target temperature; and
   operate the climate control system to regulate a container temperature to the target temperature.

17. The temperature-controlled delivery appliance of claim 16, wherein the storage container is one of a plurality of storage containers positioned within the cabinet, wherein the climate control system is configured for regulating a first storage container of the plurality of storage containers to a first temperature and a second storage container of the plurality of storage containers to a second temperature different than the first temperature.

18. A temperature-controlled delivery appliance comprising:
   a cabinet;
   a storage container positioned within the cabinet for receiving delivered items for storage;
   a door rotatably mounted to the cabinet for providing selective access to the storage container;
   a locking mechanism for selectively locking the door in a closed position; and
   a controller operably coupled to the locking mechanism, the controller being configured to:
   determine that an unlock condition has occurred; and
   unlock the locking mechanism in response to determining that the unlock condition has occurred.

19. The temperature-controlled delivery appliance of claim 18, further comprising:
   a wireless communication module in communication with a wireless network, wherein the controller is operably coupled to the wireless communication module and is configured to:
   determine that the cabinet has been moved out of range of the wireless network; and
   provide a user notification or security alert.

\* \* \* \* \*